(12) United States Patent
Wu et al.

(10) Patent No.: US 11,337,608 B2
(45) Date of Patent: May 24, 2022

(54) CONFOCAL SCANNING LASER OPHTHALMOSCOPE

(71) Applicant: SVISION IMAGING LIMITED, Henan (CN)

(72) Inventors: Heng Wu, Henan (CN); Xianzhao Peng, Henan (CN)

(73) Assignee: SVISION IMAGING LIMITED, Henan (CN)

( * ) Notice: Subject to any disclaimer, the term of this patent is extended or adjusted under 35 U.S.C. 154(b) by 272 days.

(21) Appl. No.: 16/858,699

(22) Filed: Apr. 26, 2020

(65) Prior Publication Data

US 2020/0260951 A1    Aug. 20, 2020

Related U.S. Application Data

(63) Continuation-in-part of application No. PCT/CN2018/110794, filed on Oct. 18, 2018.

(30) Foreign Application Priority Data

Oct. 25, 2017    (CN) .......................... 201711018788.9

(51) Int. Cl.
*A61B 3/12*    (2006.01)
*G02B 9/04*    (2006.01)
*A61B 3/10*    (2006.01)

(52) U.S. Cl.
CPC .............. *A61B 3/12* (2013.01); *A61B 3/1025* (2013.01); *A61B 3/1241* (2013.01); *G02B 9/04* (2013.01)

(58) Field of Classification Search
CPC .. G02B 9/04; G02B 21/0012; G02B 21/0076; G02B 21/0028; A61B 3/1025; A61B 3/12; A61B 3/1241; A61B 3/156
See application file for complete search history.

(56) References Cited

U.S. PATENT DOCUMENTS

2015/0282705 A1    10/2015    Avital

FOREIGN PATENT DOCUMENTS

| CN | 102885607 | 1/2013 |
| CN | 103926679 | 7/2014 |
| CN | 106539556 | 3/2017 |
| WO | 2011129485 | 10/2011 |
| WO | 2014048570 | 4/2014 |

*Primary Examiner* — Jack Dinh
(74) *Attorney, Agent, or Firm* — JCIP Global Inc.

(57) ABSTRACT

A confocal scanning laser ophthalmoscope (cSLO) includes an illumination module, an acquisition module, a scanning element and an imaging lens group. With the scanning element at the nominal position and the illumination beam passing through the centers of the lenses, by controlling the deviation angle between the incident marginal rays and the reflected rays on each surface of the lenses in the illumination path to no less than 0.5 degree.

20 Claims, 8 Drawing Sheets

(a)
 (b)
 (c)
 (d)
 (e)
 (f)
 (g)
 (h)
 (i)

CONFOCAL SCANNING LASER OPHTHALMOSCOPE

CROSS-REFERENCE TO RELATED APPLICATION

This application is a continuation in part of international PCT application serial no. PCT/CN2018/110794, filed on Oct. 18, 2018, which claims the priority benefit of China application no. 201711018788.9, filed on Oct. 25, 2017. The entirety of each of the above-mentioned patent applications is hereby incorporated by reference herein and made a part of this specification.

BACKGROUND

Technical Field

The invention relates to an ophthalmic imaging system, in particular to a confocal scanning laser ophthalmoscope.

Description of Related Art

Confocal scanning laser ophthalmoscopes (cSLO) are used in ophthalmic clinics routinely for retina imaging and florescence angiography as a safe imaging modality. Specifically, a cSLO uses visible or near-IR light sources to continuously scan the retina surface spot by spot. Though the name of cSLO contains the key word of "laser" as a convention, many cSLO instruments also use broadband light sources such as a superluminescent diode (SLD) to minimize speckle noise which is commonly found in imaging systems based on lasers. The scattered light from the target returns along the illumination path, after passing through a confocal pinhole, is detected by a photo detector of high sensitivity, usually a PMT (photomultiplier tube) or an APD (avalanche photo diode). After signal amplification and digitization, a computer acquires the raw data and reconstructs it into two-dimensional images. Compared with traditional ophthalmoscopes, cSLOs have the advantages of low radiation, high contrast, high collection efficiency, mydriasis-free imaging. The confocal feature of cSLOs ensures only the light returned from the focused plane in the object space is collected, thus greatly improves the contrast of the images. Besides, cSLOs can be set to receive light from a certain layer of the imaging target, making tomography possible.

cSLOs can image different lesions of retina. With infrared illumination, the pigment distribution of the retinal pigment epithelial layer can be observed. For patients with central serous retinopathy, macular holes and dry age-related macular degeneration (AMD), depigmentation can often be clearly observed by infrared light examination. For children and patients with severe photophobia and refractive interstitial opacity, it is more convenient to examine the retina with infrared light. With indocyanine green angiography (ICGA), the filling process and morphology of choroidal vessels are more readily visible than infrared illumination without fluorescence agent.

In the optical design of cSLOs for retina imaging, due to the limited size of the eye pupil and thus the extremely low collection efficiency of retina reflection and scattering, the energy which can be received by a detector could be overshined by the reflected stray light from the pupil or the lens surfaces, even though the optical surfaces are usually AR-coated Although the confocal nature of the cSLO system can effectively suppress the stray light from out-of-focus planes e and most reflection from off-center points, the central reflection of the lens surfaces can still reach the detector and result in a very bright spot at the center of the cSLO images. As shown in FIG. 1 from the cSLO device described in "Optimization of confocal scanning laser ophthalmoscope design" (Francesco LaRocca, Al-Hafeez Dhalla, Michael P. Kelly, Sina Farsiu, and Joseph A. Izatt), Journal of Biomedical Optics 18(7), 076015 (July 2013), the lens reflection results in a very bright spot in the image center. The authors used background subtraction algorithm to remove the ghosting spots and obtained the corrected image as shown in FIG. 2.

The problem of lens reflection is especially prominent for cSLO systems with large FOV. For example, "Scanning Laser Ophthalmoscopy and Angiography with a Wide-Field Contact Lens System" (Staurenghi G, Viola F, Mainster M A, Graham R D, Harrington P G, Arch Ophthalmol. 2005; 123(2):244-252. doi:10.1001/archopht.123.2.244) introduces a contact type of cSLO with large FOV on human eyes. The drawings and text comparison in the document show that the influence of lens reflection on images can be ignored due to the use of filters in ICGA (most retina images except FIG. 5 in that document). However, in the infrared cSLO image without fluorescence, lens reflection is not suppressed by the fluorescence filters, and the influence of lens reflection can still be clearly seen in the retina images, as shown in FIG. 3.

This is because: 1. To achieve larger field of view (FOV), the ratio of the effective focal length (EFL) of the scan lens over the ocular lens has to be higher than the cases of small or moderate FOV. With a given ocular lens, the EFL of the scan lens must be longer, resulting in a smaller numerical aperture (NA) when the reflected stray light propagating back to the receiver fiber tip is concerned. the more the reflected ray bundle resembles a parallel beam before reaching the collimator of the collection module, the more likely the stray light is coupled into the receiver fiber and incurs ghosting. 2. The optical design with large FOV results in more lenses, which increases the chance that a surface happens to fall on the conjugate of the fiber tip (whose core acts as the confocal pinhole) and thus generating significant ghosting.

U.S. Pat. No. 9,204,791 introduces an optical design of cSLO in which a cylindrical mirror is arranged at the conjugate position of the retina. In order to avoid the surface reflection, the lens is tilted to keep reflected stray light away from the optical path of retina imaging.

The main characteristics of ghosting present in the central area of cSLO images are as follows: 1. cSLO illumination light passes through some of the optical surfaces in the system twice in opposite directions, so the source of the ghosting is mainly the primary reflection of optical surfaces; and 2. In cSLO systems using a collimator and a fiber in the collection module, the core diameter of optical fiber at the acquisition end effectively serves as the pinhole of the confocal system, and it is the stray light near the centers of the lenses which is reflected and tends to cause ghosting in the image.

The FOV on commercial cSLO instruments has been increasing in recent years. The widefield cSLOs bring great convenience for diagnosis of retina diseases especially the lesions in the peripheral areas. But the scanning angle range of the scanning element is limited under the premise of high-speed scanning, so the angle amplification must be increased to cover larger FOV and the beam size at the entrance pupil of the scan lens has to be increased accordingly in order to maintain similar lateral resolution. When the beam size becomes large, the confocal pinhole is less effective in suppressing the central ghosting, thus making optical design more challenging. A method for suppressing stray light by tilting or shifting optical elements as in U.S. Pat. No. 9,204,791 is widely used in ophthalmic examination equipment. The method of tilting or shifting optical elements is relatively effective for planar optical elements, but for optical elements with non-zero optical power, it also incurs degradation of imaging quality and decrease of light throughput. For ophthalmic cSLO systems with a FOV exceeding 30 degrees, it is difficult to completely remove ghosting by tilting the optical elements without compromising the image quality.

SUMMARY

Purpose of the Invention: To solve the problems existing in the prior arts and reduce the stray light caused by central reflection from lens surfaces. The invention provides an optical design of a cSLO with very low ghosting.

Technical scheme: A confocal scanning laser ophthalmoscope includes an illumination module, an acquisition module, a scanning element and an imaging lens group, wherein the illumination module is used to emit a collimated light beam, wherein the light source could be a narrow-band light source such as a laser, or a broadband light source such as a SLD; the imaging lens group includes an ocular lens, a first lens group, a reflective or dichroic mirror and a second lens group; after passing through the scanning element, the collimated light beam passes sequentially through the second lens group, the reflective or dichroic mirror, the first lens group and the ocular lens before reaching the retina, and then the reflected and scattered light returns to the acquisition module; the acquisition module includes optical fibers, which are used for collecting the returned light from the imaging target. In the optical design, at the centers of all lens surfaces along the illumination path, the deviation angle between the incident marginal rays and reflected rays is kept no less than 0.5 degree.

Beneficial effects: according to the cSLO of the invention, the scanning FOV in front of eyes covers a wide field of 40°×40°. The chromatic aberration is corrected in the spectral range of 770 nm to 860 nm, covering the waveband of near-IR illumination and the working waveband of ICGA, that is, the said system can be used for both near-IR cSLO imaging or ICGA imaging, and could be extended to visible waveband as well. The optical design of the cSLO is particularly optimized by restricting the deviation angle of the light at the centers of the lens-air interfaces or the interfaces of lenses of different materials, the residual reflection is effectively suppressed from reaching the detector, and thus the center ghosting is minimized.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

Figure 9:
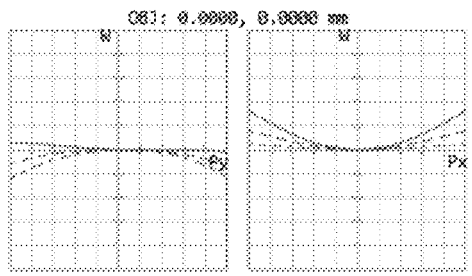
Figure 9:
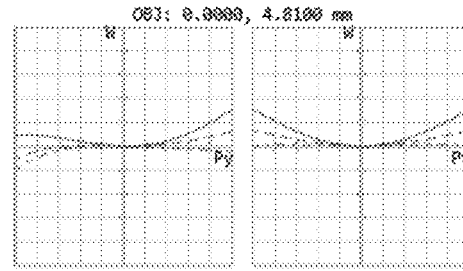
Figure 9:
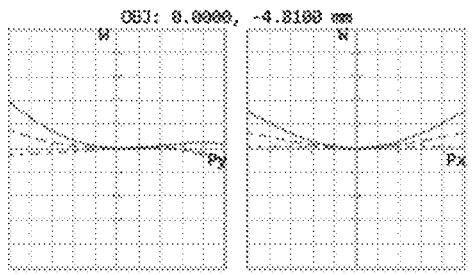
Figure 9:
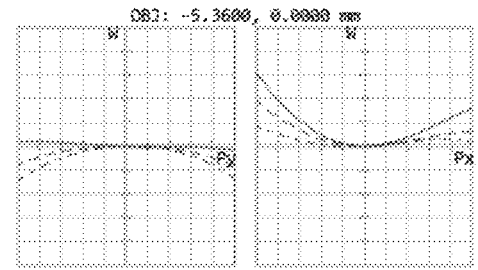
Figure 9:
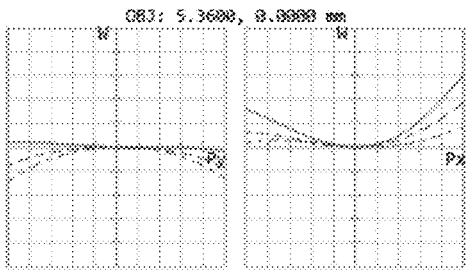
Figure 9:
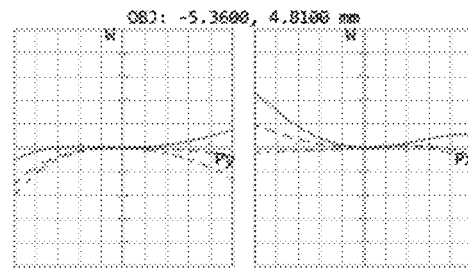
Figure 9:
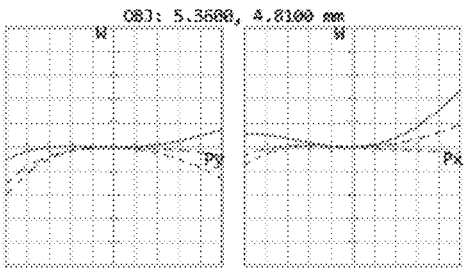
Figure 9:
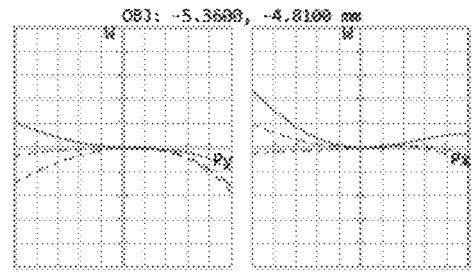
Figure 9:
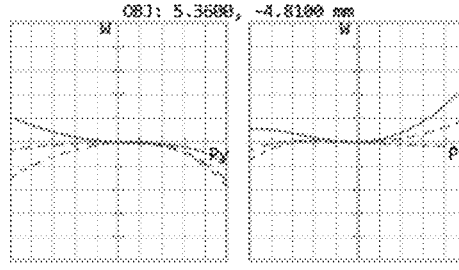
Figure 10:
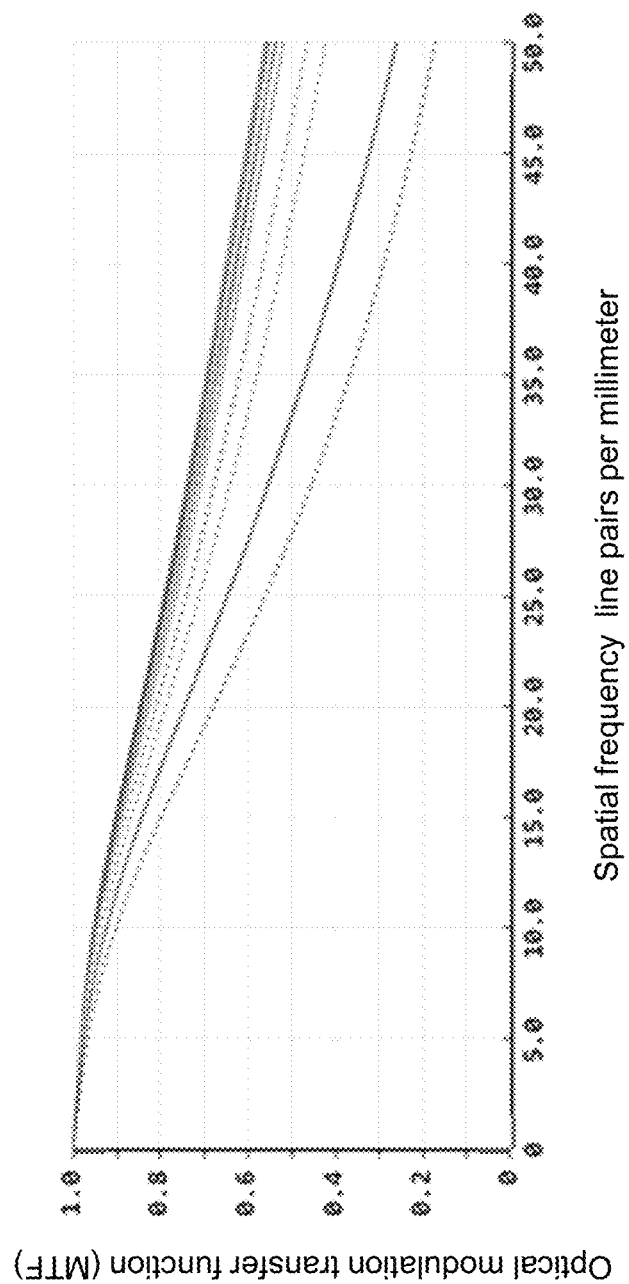

(a) of FIG. 9 is the wavefront error diagram of the first field point in the present embodiment;

(b) of FIG. 9 is the wavefront error diagram of the second field point in the present embodiment;

(c) of FIG. 9 is the wavefront error diagram of the third field point in the present embodiment;

(d) of FIG. 9 is the wavefront error diagram of the fourth field point in the present embodiment;

(e) of FIG. 9 is the wavefront error diagram of the fifth field point in the present embodiment;

(f) of FIG. 9 is the wavefront error diagram of the sixth field in the present embodiment;

(g) of FIG. 9 is the wavefront error diagram of the seventh field point in the present embodiment;

(h) of FIG. 9 is the wavefront error diagram of the eighth field point in the present embodiment;

(i) of FIG. 9 is the wavefront error diagram of the ninth field point in the present embodiment; and FIG. 10 is the modulation transfer function (MTF) diagram of the present embodiment.

DESCRIPTION OF THE EMBODIMENTS

The present invention will be further described below with reference to the accompanying drawings and specific embodiments.

Figure 4:
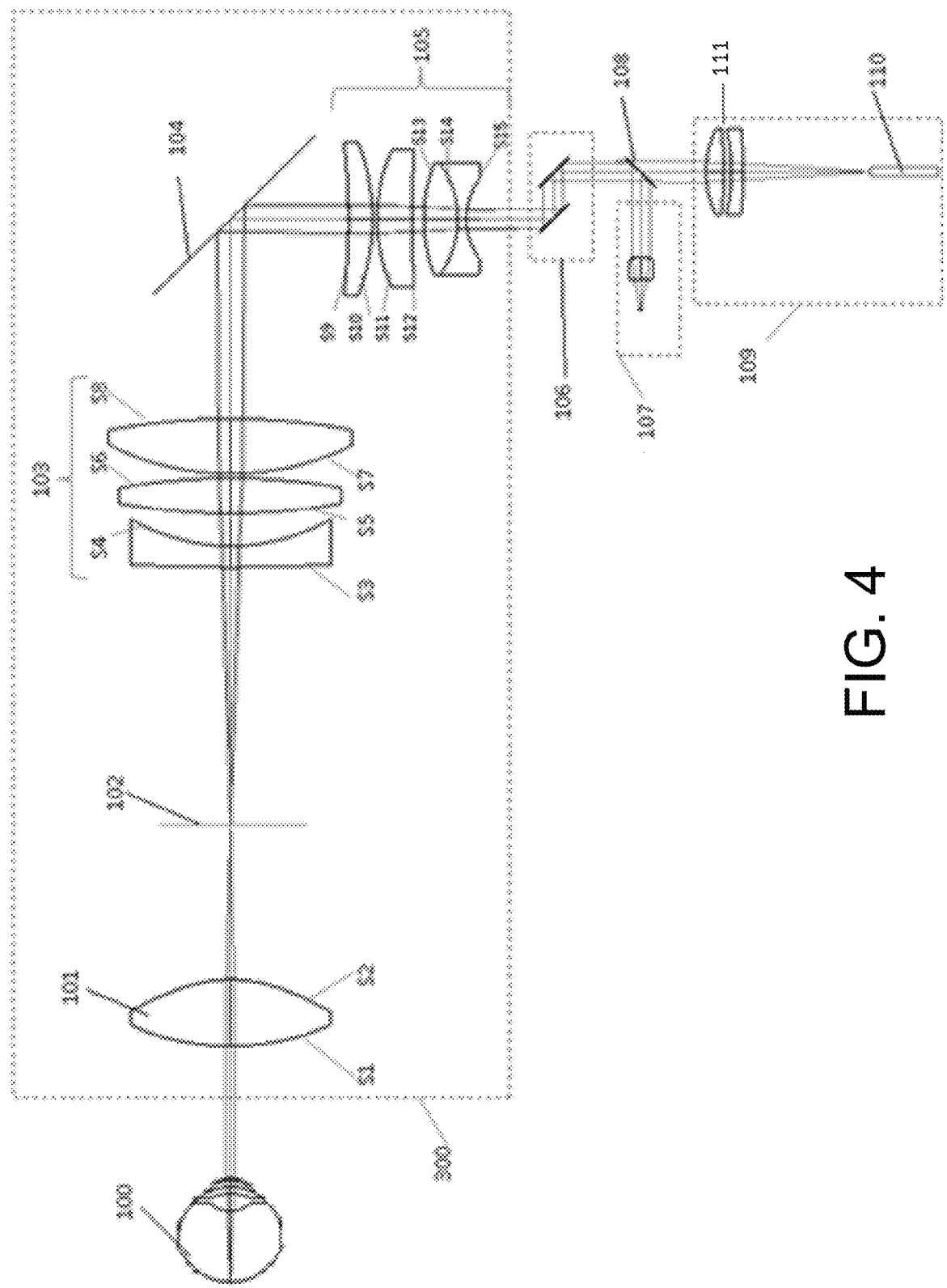
FIG. 4 is an optical system diagram of a confocal scanning laser ophthalmoscope.

As shown in FIG. 4, a confocal scanning laser ophthalmoscope (cSLO) includes an illumination module 107, an acquisition module 109, a scanning element 106 and an imaging lens group 300. The illumination module 107 is used to emit a collimated light beam, wherein the illumination module 107 includes a light source and the light source could be a narrow-band light source such as a laser, or a broadband light source such as a SLD. The imaging lens group includes an ocular lens 101, an intermediate image plane 102, a first lens group 103, a reflective or dichroic mirror 104 and a second lens group 105.

The illumination module 107 generates a collimated illumination beam. The illumination beam goes through a beam splitter 108 then enters the scanning element 106, then it passes through the second lens group 105 and is reflected by the reflective or dichroic mirror 104, then it goes through the first lens group 103, the ocular lens 101, enters the eye under test and eventually reaches the retina 100. The reflected and scattered light from the retina 100 then come back along the original illumination path, specially, it passes sequentially through the eye, the ocular lens 101, the first lens group 103, the reflective or dichroic mirror 104, and the second lens group 105, the scanning element 106, the beam splitter 108, the collection lens 111 before reaching the end face of the optical fiber in the acquisition module 109, which includes a collection lens group 111 and an optical fiber 110 for collecting the returned light, thereby the returned light is detected and converted to electrical signal.

Figure 8:
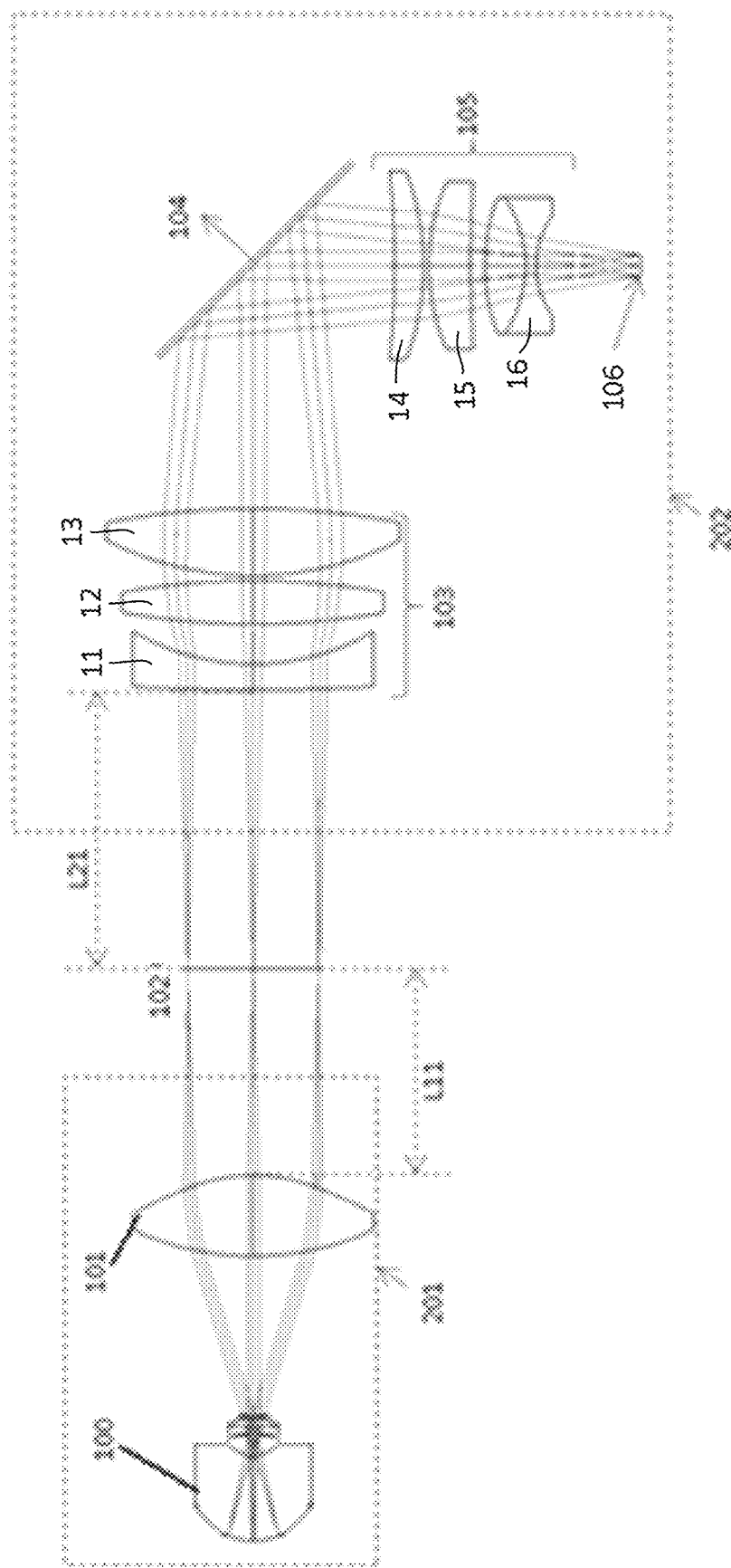
FIG. 8 is a schematic diagram of the common optical path shared by both illumination and collection of the cSLO in the present embodiment.

Specifically, as shown in FIG. 8, the ocular lens 101 is a biconvex aspheric lens. The first lens group 103, the reflective or dichroic mirror 104 and the lens group 105 constitute a scan lens group 202. The first lens group 103 includes a lens 11, a lens 12, and a lens 13. The cSLO system in the present embodiment covers a large FOV of 40°×40° (measured in front of the eyes), so it is important to balance field curvature. Lens 11 is a negative lens close to the intermediate image plane 102 to balance field curvature, and the concave center thereof is on the side away from the ocular lens. Lens 12 and lens 13 are both biconvex positive lenses. The incident angle of the illumination light in the edge field on the reflective or dichroic mirror 104 is well-controlled by balancing the optical power of lens 11, lens 12 and lens 13, to reduce the manufacturing difficulty of the dichromic mirror. The second lens group 105 includes a lens 14, a lens 15, and a lens 16. Lens 14 is a meniscus lens with both concave centers on the side away from the scanning element. Lens 15 is a near-plano-convex positive lens. Lens 16 is a meniscus doublet lens next to the scanning element. The two concave centers thereof are both on the side close to the scanning element. The doublet design corrects most of the chromatic aberration in the cSLO path to ensure the optical performance in near-infrared and ICGA wavebands. The scanning element 106 is placed at the entrance pupil of the scan lens group 202.

The angle deviation, in the context of this invention, is defined as the angle between an incident ray and its reflected rays on a lens surface. In the optical design of this invention, with the scanning element at its nominal position where the illumination beam goes along the optical axis, the deviation angle of the marginal rays on any non-zero-power element is constrained to be no less than 0.5 degree, that is, the deviation angle of the marginal rays of the illumination beam at the centers of each surface of the ocular lens 101, the first lens group 103 and the second lens group 105 is no less than 0.5 degree.

In the optical design of the cSLO, the optical path from the beam splitter 108 to the human eye is the common optical path 300 of illumination and collection. Light reflected by the surfaces of the lenses in the common optical path 300 is more likely to enter the optical fibers 110 and form a bright ghosting spot near the image center, whereas the reflection of the lenses in the illumination module 107 and the acquisition module 109 has little effect. Therefore, the present embodiment only needs to limit the angle deviation of the marginal rays of the illumination beam at the centers of the non-zero power lenses in the common optical path 300.

Figure 5:
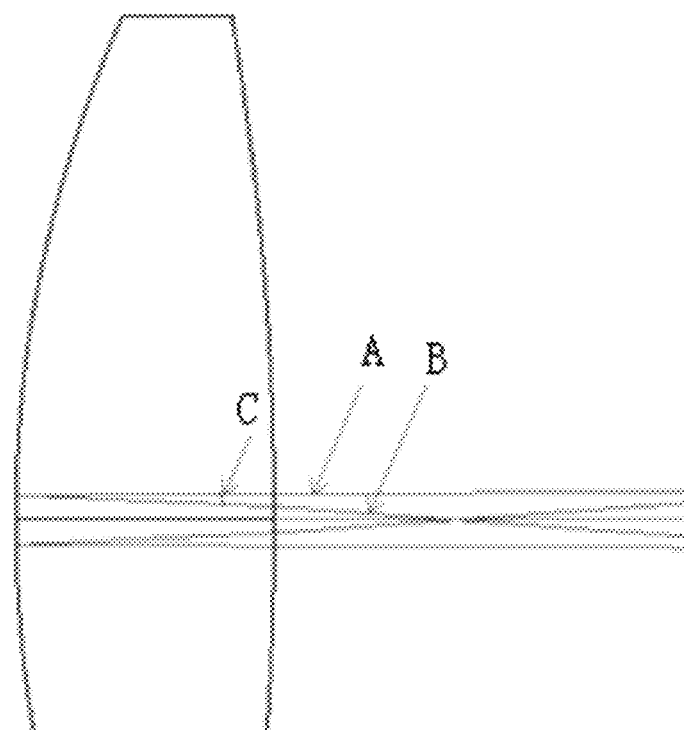
FIG. 5 is a schematic diagram of angle deviation of reflected stray light.

The following is a stray light analysis for the lenses in the common optical path 300:

As shown in FIG. 5, the direction from the scanning element to the retina is the incident illumination light direction, labeled as A in the figure, and the corresponding incident angle is i; and the reflection angle corresponding to the surface reflection of the lens is i', that is, the reflection direction is labeled as B in the figure, and the angle deviation (i.e. C in the figure) between the two is defined as:

$$\text{Angle deviation} = i - i' \quad (1)$$

Due to the limited numerical aperture of the optical fiber, only the stray light ghosting within a small central area can enter the optical fiber. In the paraxial approximation regime, for a single optical surface with a fixed position in the optical path, the larger the angle deviation of the reflected light from the incident light, the less likely it is to generate ghosting. The illumination beam going through the lens centers is of particular concern since theoretically the principal ray of the illumination ray bundle always results a zero deviation angle at the center of the lens surfaces and comes back to the fiber core along the original path. The marginal ray, in comparison, will be reflected at a non-zero angle. To evaluate how much central ghosting a certain surface will cause, the deviation angle of the marginal ray can serve as an indicator and a quantitative analysis is necessary.

Figure 1:
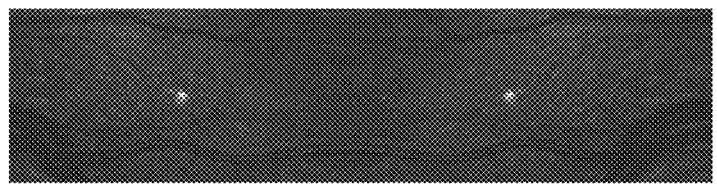
FIG. 1 is an image with ghosting spots.
Figure 2:
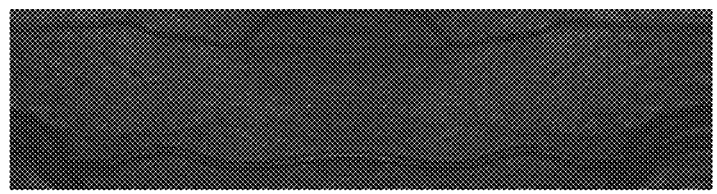
FIG. 2 is an image with ghosting spots removed.
Figure 3:
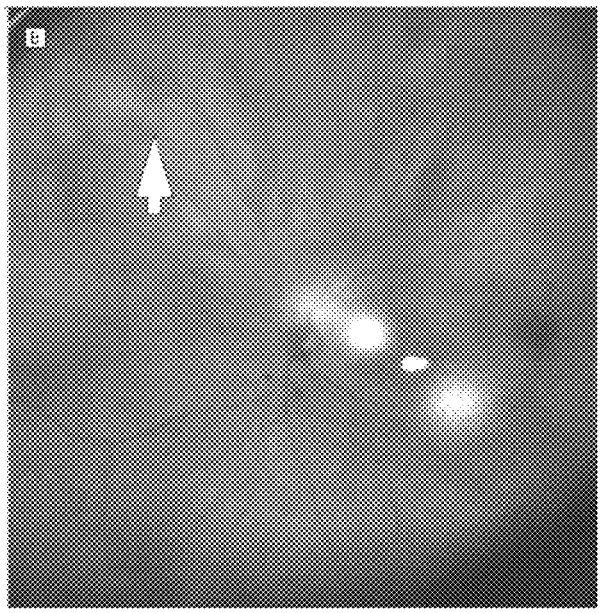
FIG. 3 is an infrared cSLO image of a retina with ghosting from lens reflections.

The angle deviation of the marginal rays on the lens surfaces S1-S15 in FIG. 1 is shown in Table 1.

TABLE 1

| Angle Deviation in 0-degree Scanning FOV | |
|---|---|
| Surface Label | Angle deviation Degree |
| S1 | 2.4 |
| S2 | 4.6 |
| S3 | 3.5 |
| S4 | 5.5 |
| S5 | 7.2 |
| S6 | 1.3 |
| S7 | 7.8 |
| S8 | 0.6 |
| S9 | 1.2 |
| S10 | 5.5 |
| S11 | 6.6 |
| S12 | 2.4 |
| S13 | 3.1 |
| S14 | 16.2 |
| S15 | 9.1 |

Figure 6:
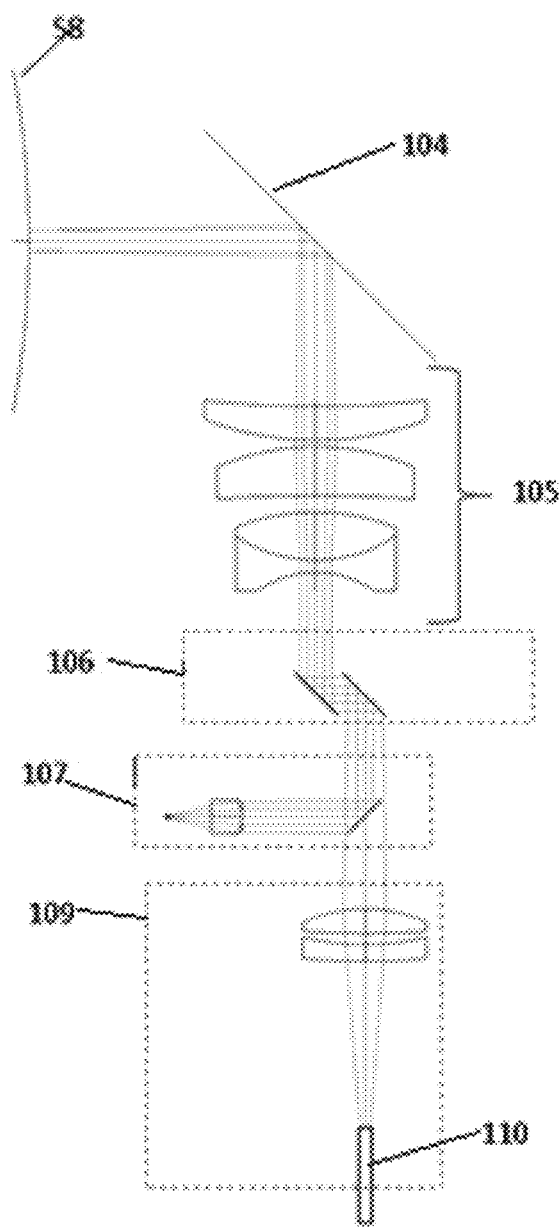
FIG. 6 is a schematic diagram of the central reflection of lens surface S8 in the embodiment.
Figure 7:
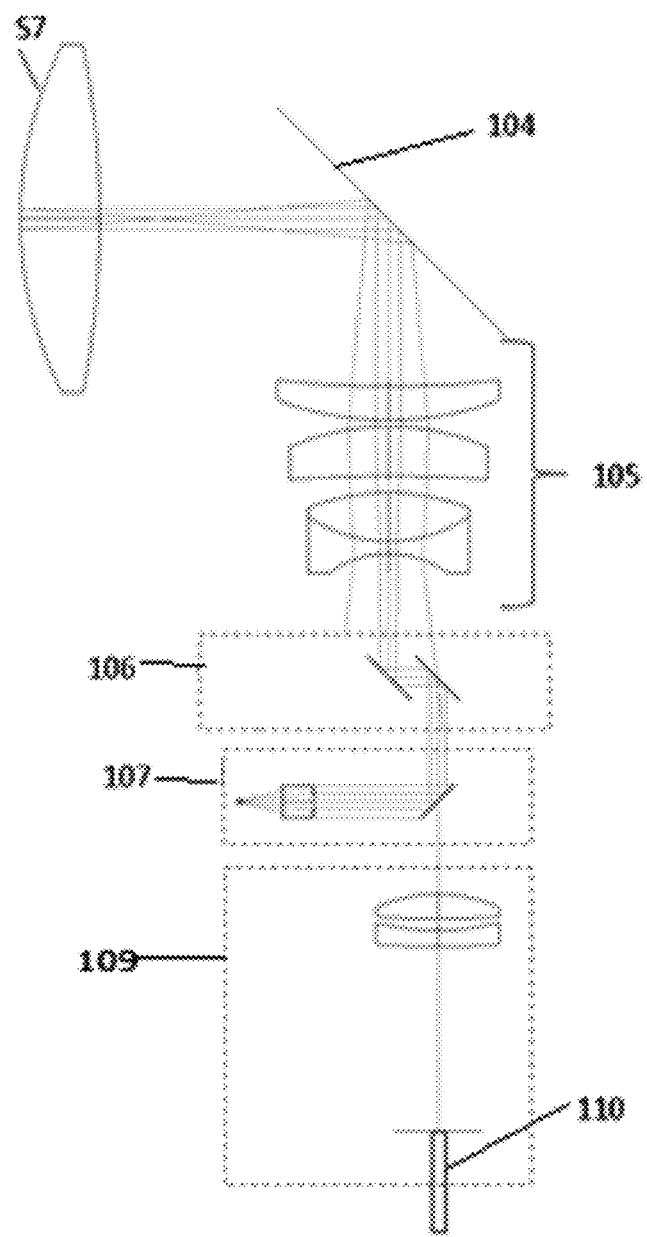
FIG. 7 is a schematic diagram of the central reflection of lens surface S7 in the embodiment.

As shown in Table 1, S8 is theoretically the surface of the worst offender for ghosting as suggested by the smallest angle deviation of the marginal rays. Ghosting analysis based on angle deviation of marginal rays can also be verified by tracing the stray light from lens surface reflection ghosting. FIG. 6 shows stray light ray-tracing on surface S8 and FIG. 7 shows the stray light ray-tracing on Surface S7. Comparing FIG. 6 and FIG. 7, it can be seen that the ghosting from surface S8 is more effectively collected by the detector through the collection fiber and causes a ghosting at the image center. This ray tracing simulation is consistent with the results in Table 1.

Besides design constraints, anti-reflection coating can reduce the lens reflection from 4%-5% to 0.5% or less, and 0.1%-0.2% for small incident angles less than 6°. Further analysis shows the worst offender surface S8 will 0.45% of illumination light will return and couple into the acquisition module if the reflection of the surface were 100%. With a AR coating of 0.2%, there will be $9 \times 10^{-6}$ of the illumination light coming back and results in a central ghosting that is 1% of the highest intensity of the cSLO image. The residual ghosting could be easily corrected by a simple background subtraction.

The distance between the ocular lens and the first lens group are adjustable. Through the relative movement of the ocular and the first lens group lens, the different refractive errors of the eyes under test can be compensated. There exists an intermediate image between the ocular lens and the first lens group. The intermediate image is of a telecentric design, so that there is no change in magnification and distortion during diopter compensation.

In order to accommodate a compensation range of ±20 diopters, the optical design satisfies the following constraints:

$$0.7 < L_{11}/f_{101}; \text{ and}$$

$$0.7 < L_{21}/f_{101}.$$

where $f_{101}$ is the EFL of the ocular lens, $L_{11}$ is the distance between the ocular lens and the intermediate image plane, and $L_{21}$ is the distance between the intermediate image plane and the first lens group.

In order to achieve a large FOV of 40°×40° (measured in front of the eye), it is necessary to balance field curvature. To achieve that, the first lens group includes at least one negative lens, which is located on the side, close to the ocular lens, of the first lens group, and at least one concave center of the negative lens is located on the side away from the ocular lens.

The cSLO system of the present embodiment is optically corrected for a spectral range of 770 nm to 860 nm, covering not only the waveband of the traditional near-infrared cSLO operate in, but also the waveband of indocyanine green angiography (ICGA), that is, both near-infrared or infrared narrow-band light sources and ICGA can be used for imaging the retina. At least one doublet is employed to balance chromatic aberration, and the doublet is close to the scanning element of the cSLO lens system.

Further the scan angle of the scanning element is limited under the premise of high-speed scanning. In order to cover a large FOV, in the present embodiment, the ratio of the EFLs of the ocular lens (101) and the cSLO scan (202) lens group satisfies the following constraints:

$$1.7 < f_{202}/f_{101}$$

The image quality of the optical design of the present embodiment in the spectral range of 770 nm to 860 nm are shown in the wavefront error diagrams of FIG. 9. The modulation transfer function (MTF) results in the same spectral range are shown in FIG. 10. The MTF meet the retina resolution requirements of 15 μm to 20 μm in the full FOV.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A confocal scanning laser ophthalmoscope, comprising an illumination module, an acquisition module, a scanning element and an imaging lens group, wherein,
the illumination module is used for emit a collimated light beam, wherein a light source of the illumination module comprises a narrow-band light source such as a laser, or a broadband light source such as a SLD;
the imaging lens group comprises an ocular lens, a first lens group, a reflective or dichroic mirror and a second lens group;
after passing through the scanning element, the collimated light beam passes sequentially through the second lens group, the reflective or dichroic mirror, the first lens group and the ocular lens before reaching the retina, and then the reflected and scattered light returns to the acquisition module;
the acquisition module comprises optical fibers, which are used for collecting the returned light from the imaging target; and at lens surface centers, the deviation angle between the incident marginal rays and reflected rays on all surfaces of the ocular lens, the first lens group and the second lens group is no less than 0.5 degree.

2. The confocal scanning laser ophthalmoscope according to claim 1, wherein an intermediate image plane exists between the ocular lens and the first lens group, and the intermediate image plane is telecentric.

3. The confocal scanning laser ophthalmoscope according to claim 2, wherein the distance between the ocular lens and the first lens group is adjustable.

4. The confocal scanning laser ophthalmoscope according to claim 3, wherein the ratio of the distance between the ocular lens and the intermediate image plane $L_{11}$ over the effective focal length of the ocular lens $f_{101}$ is higher than 0.7, and the ratio of the distance between the intermediate image plane and the first lens group $L_{21}$, over $f_{101}$ is also higher than 0.7, as expressed in the following inequations:

$$0.7 < L_{11}/f_{101}; \text{ and}$$

$$0.7 < L_{21}/f_{101}.$$

5. The confocal scanning laser ophthalmoscope according to claim 1, wherein the ocular lens is a biconvex aspheric lens.

6. The confocal scanning laser ophthalmoscope according to claim 2, wherein the ocular lens is a biconvex aspheric lens.

7. The confocal scanning laser ophthalmoscope according to claim 3, wherein the ocular lens is a biconvex aspheric lens.

8. The confocal scanning laser ophthalmoscope according to claim 4, wherein the ocular lens is a biconvex aspheric lens.

9. The confocal scanning laser ophthalmoscope according to claim 1, wherein the first lens group comprises at least one negative lens, the negative lens is located on a side close to the ocular lens of the first lens group, and at least one concave center of the negative lens is located on a side away from the ocular lens.

10. The confocal scanning laser ophthalmoscope according to claim 2, wherein the first lens group comprises at least one negative lens, the negative lens is located on a side, close to the ocular lens, of the first lens group, and at least one concave center of the negative lens is located on a side away from the ocular lens.

11. The confocal scanning laser ophthalmoscope according to claim 3, the first lens group comprises at least one negative lens, the negative lens is located on a side, close to the ocular lens, of the first lens group, and at least one concave center of the negative lens is located on a side away from the ocular lens.

12. The confocal scanning laser ophthalmoscope according to claim 4, wherein the first lens group comprises at least one negative lens, the negative lens is located on a side, close to the ocular lens, of the first lens group, and at least one concave center of the negative lens is located on a side away from the ocular lens.

13. The confocal scanning laser ophthalmoscope according to claim 1, wherein the second lens group comprises at least one meniscus doublet lens, and the concave centers of the two surfaces of the meniscus doublet lens are both on a side close to the scanning element.

14. The confocal scanning laser ophthalmoscope according to claim 2, wherein the second lens group comprises at least one meniscus doublet lens, and the concave centers of the two surfaces of the meniscus doublet lens are both on a side close to the scanning element.

15. The confocal scanning laser ophthalmoscope according to claim 3, wherein the second lens group comprises at least one meniscus doublet lens, and the concave centers of the two surfaces of the meniscus doublet lens are both on a side close to the scanning element.

16. The confocal scanning laser ophthalmoscope according to claim 4, wherein the second lens group comprises at least one meniscus doublet lens, and the concave centers of the two surfaces of the meniscus doublet lens are both on a side close to the scanning element.

17. The confocal scanning laser ophthalmoscope according to claim 1, wherein the ratio of the effective focal length of the imaging lens group $f_{202}$ over the effective focal length of the ocular lens $f_{101}$ is higher than 1.7, as expressed in the following inequation:

$$1.7 < f_{202}/f_{101}.$$

18. The confocal scanning laser ophthalmoscope according to claim 2, wherein the ratio of the effective focal length of the imaging lens group, and the second lens group, $f_{202}$ over an effective focal length of the ocular lens $f_{101}$ is higher than 1.7, as expressed in the following inequation:

$$1.7 < f_{202}/f_{101}.$$

19. The confocal scanning laser ophthalmoscope according to claim 1, wherein the confocal scanning laser ophthalmoscope is used for visible, near infrared or infrared imaging.

20. The confocal scanning laser ophthalmoscope according to claim 1, wherein the foresaid apparatus is used for ICGA imaging.

* * * * *